United States Patent [19]
Ramirez Jimenez

[11] Patent Number: 5,458,641
[45] Date of Patent: Oct. 17, 1995

[54] VERTEBRAL BODY PROSTHESIS

[76] Inventor: Juan J. Ramirez Jimenez, Calle Rio Parana No. 1376, Col. Olimpica S.R., C.P. 44430, Guadalarjara, Jalisco, Mexico

[21] Appl. No.: 117,619

[22] Filed: Sep. 8, 1993

[51] Int. Cl.$^6$ .................................................. A61F 2/44
[52] U.S. Cl. ........................... 623/17; 606/61; 403/43
[58] Field of Search ........................... 623/17; 606/61; 403/43–44

[56] References Cited

U.S. PATENT DOCUMENTS

| | | | |
|---|---|---|---|
| 4,289,123 | 9/1981 | Dunn | 623/17 X |
| 4,401,112 | 8/1983 | Rezaian | 623/17 X |
| 4,445,513 | 5/1984 | Ulrich et al. | 606/61 |
| 4,553,273 | 11/1985 | Wu | 623/18 |
| 4,611,582 | 9/1986 | Duff | 606/61 |
| 4,657,550 | 4/1987 | Daher | 623/17 |
| 5,201,734 | 4/1993 | Cozad et al. | 606/62 |

FOREIGN PATENT DOCUMENTS

| | | | |
|---|---|---|---|
| 3729600 | 3/1989 | Germany | 623/17 |
| 0072056 | 6/1977 | Japan | 403/43 |
| 4114644 | 4/1992 | Japan | 623/17 |

*Primary Examiner*—David H. Willse
*Attorney, Agent, or Firm*—Nixon & Vanderhye

[57] ABSTRACT

The vertebral body prosthesis includes cephalic and caudal components with a separating setscrew therebetween. The cephalic component includes a generally horizontal member having an upper porous, water-permeable surface complementary shaped to the underside of the adjacent vertebral body, a securement element upstanding along one side for receiving screws to secure the cephalic component to the upper vertebral body and a depending guide element. The lower caudal component includes a generally horizontally disposed member having a porous, water-permeable undersurface complementary shaped to the upper surface of the lower adjacent vertebral body, a depending securement element along one side for receiving screws to secure the caudal component to the lower vertebral body and an upstanding guide element for engaging the depending guide element of the cephalic component to prevent rotation of the components. A separating setscrew is disposed between the members of the components and is adjustable to adjustably space the components relative to one another whereby a vertebral body prosthesis is formed.

9 Claims, 4 Drawing Sheets

VERTEBRAL BODY PROSTHESIS

TECHNICAL FIELD

The present invention relates to a prosthesis for the human spine and particularly relates to a vertebral body prosthesis for replacing a removed vertebral body and supporting the vertebrae.

BACKGROUND

Prostheses for various implantation systems are, of course, well known. For those individuals, however, experiencing serious spinal ailments and infirmities, very little has been accomplished in the nature of prosthetic devices for use in the vertebral column. Thus, patients having primary and/or metastatic malignant tumors not responding to other therapy, or experiencing intense and persistent backbone pain caused by tumorous vertebrae, or spinal cord compression with paresis or paraplegia, or having vertebral collapse or backbone instability, have not heretofore had available to them a prosthesis for alleviating these maladies.

DISCLOSURE OF THE INVENTION

According to the present invention, there is provided a prosthesis for the replacement of a vertebral body in the human spinal column which can alleviate pain and spinal cord decompression, stabilize the vertebrae, facilitate anatomical recovery and can be integrated biologically. The present prosthesis immediately relieves pain, permits removal of a tumorous vertebral body, does not require osseous cement or grafting, provides immediate backbone stability, facilitates and allows radio and chemotherapy to the primary tumor and can be implanted in a simple and rapid operation.

To accomplish the foregoing, the present invention provides a prosthesis formed of essentially three components: a cephalic or proximal component, a caudal or distal component and a columnar separator setscrew or sleeve component for adjustably spacing the cephalic and caudal components. The cephalic component includes a generally horizontally disposed member having an upper surface shaped generally complementary to the undersurface of an upper vertebral body, an element upstanding from and to one side of the member having vertically and laterally spaced openings, preferably angled relative to one another, for receiving screws to secure the cephalic component to the upper vertebral body, and a guide element depending from the member for connection with the caudal component. The caudal component has a generally horizontally disposed member having a lower surface shaped generally complementary to the upper surface of a lower vertebral body, a guide element upstanding from the lower member along one side thereof for engagement with the depending guide element of the cephalic component, and an element depending from the lower member and having vertically and laterally spaced openings, preferably angled relative to one another, to receive screws for securing the caudal component to the lower vertebral body. The cephalic component has a centrally disposed, externally threaded pin depending from the cephalic member, while the caudal element has an externally threaded pin upstanding from the caudal member. The separator component comprises a setscrew, i.e., an internally threaded sleeve for threaded engagement at its opposite ends with the pins. The separator sleeve component enables the components to be displaced toward and away from one another.

In a preferred form, the depending guide element of the cephalic component includes a recess for receiving an upstanding guide element of the lower caudal member. These guide elements are shaped to prevent relative rotation of the cephalic and caudal components. Set screws are employed to maintain the cephalic and caudal components in adjusted spaced positions relative to one another. It will be appreciated that the guide elements can be reversed, i.e., the upstanding guide on the caudal element may have the recess, while the depending guide element of the cephalic element may project for reception in the recess.

As mentioned above, the surfaces of the members in contact with the vertebral bodies are substantially complementary in shape to the vertebral body surfaces and are preferably porous and permeable to facilitate osseous growth in the parts of the surfaces that contact the vertebral bodies. The surfaces thus offer favorable conditions for bone growth within the prosthesis and may comprise any one of hydroxyapatite, a ceramic, polymer, metals and cobalt alloys. Preferably, a titanium alloy with a 5–50 micron rough surface to facilitate biological integration in the form of a porous coating of a thickness of approximately 0.5 mm to 3 mm is used.

In an alternate embodiment, the surface in contact with the vertebral body may be crowned with projections for reception in corresponding recesses in the vertebral body. For example, generally cone-shaped projections spaced one from the other about the members may be employed.

To employ the prosthesis of the present invention, the diseased or malignant vertebral body is removed, along with the inter-vertebral fibro-cartilages. The prosthesis is preassembled by inserting the guide element of the caudal component into the recess of the cephalic component with the threaded setscrew or sleeve engaging the threaded pins on the members of the components. With the prosthesis preassembled, the members of the components are inserted between the vertebral bodies adjacent the removed vertebral body, with the upstanding and depending elements of the cephalic and caudal components, respectively, lying to one side of the adjacent vertebral body. The setscrew or sleeve is then rotated to space the cephalic and caudal components until the surfaces of the members engage in the complementary-shaped surfaces of the adjacent vertebral bodies. Screws are passed through the openings of the upstanding and depending elements of the components and threaded into the vertebral bodies. Once fixed, the set screws on the depending element of the cephalic component are tightened to secure the components against rotation relative to one another.

In a preferred embodiment according to the present invention, there is provided a prosthesis for replacing a vertebral body in the spine of a human being comprising a cephalic component including a generally horizontally disposed member having an upper surface for engaging the underside of an upper vertebral body, a caudal component including a generally horizontally disposed member having a lower surface for engaging the upper side of a lower vertebral body and means for connecting the components in selected adjusted positions relative to one another, whereby stabilization of and support for the spine is afforded.

In a further preferred embodiment according to the present invention, there is provided a prosthesis for replacement of a vertebral body comprising a cephalic component having a first member for engaging the underside of an upper vertebral body, an element upstanding from and on one side of the member for securement to a lateral side of the upper vertebral body and a guide element depending from the member. A caudal component has a second member for engaging the upper side of an lower vertebral body, an element depending from the second member for securement to a lateral side of the lower vertebral body and a guide element upstanding from the second member, the guide elements being engageable with one another, enabling movement of the members toward and away from one another. Means are provided for connecting the guide elements to one another for preventing rotational movement of the components relative to one another.

In a still further preferred embodiment according to the present invention, there is provided a vertebral body prosthesis comprising a cephalic component having a member for engaging the underside of an upper vertebral body, a caudal component having a member for engaging the upper side of a lower vertebral body and an element carried by each of the components along corresponding sides and engageable with one another cooperatively, enabling adjusting movement of the members toward and away from one another and preventing rotational movement of the components relative to one another. An adjustment mechanism is provided cooperable between the components for locking the components in selected adjusted spaced positions relative to one another.

Accordingly, it is a primary object of the present invention to provide a novel and improved vertebral body prosthesis for replacing a diseased or malignant vertebral body.

BEST MODE FOR CARRYING OUT THE INVENTION

Reference will now be made in detail to a present preferred embodiment of the invention, an example of which is illustrated in the accompanying drawings.

Figure 1:
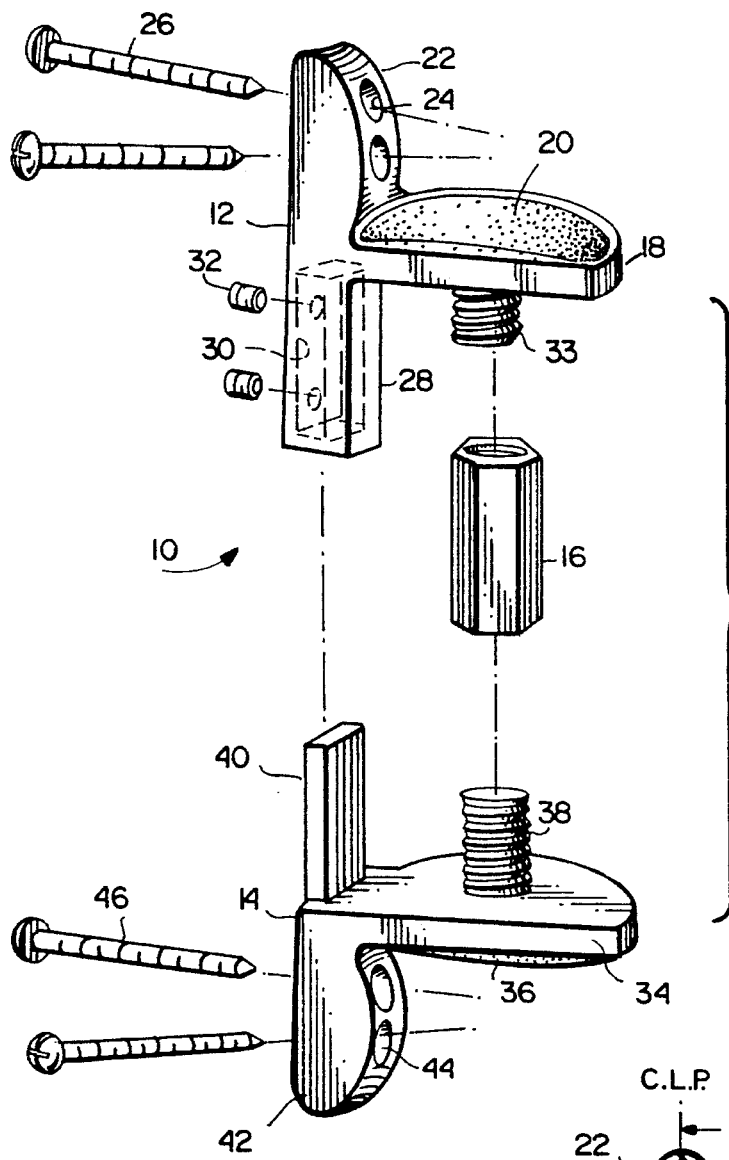
FIG. 1 is an exploded perspective view of a vertebral body prosthesis according to the present invention illustrating the cephalic and caudal components, as well as the separator sleeve.

Referring now to the drawings, particularly to FIG. 1, there is illustrated a vertebral body prosthesis according to the present invention, generally indicated 10. Prosthesis 10 includes essentially three components, namely a cephalic or proximal component 12, a caudal or distal component 14 and a separating setscrew or sleeve 16. Turning first to the cephalic component 12, it includes a generally horizontally disposed member 18 having a generally semi-circular configuration in plan, with an upper surface 20 for engaging the underside of an upper vertebral body. Cephalic component 12 also includes an element 22 upstanding from the member 18 and along one side thereof and having two or more screw holes 24 opening laterally for receiving screws 26 to secure the cephalic component to the vertebrae, as described below. As illustrated, the screw holes 24 are vertically and laterally spaced from one another and angled relative to one another. A guide element 28 depends from the member 18 in alignment with element 22. Guide element 28 has a recess 30 opening through its lower end and which recess has a multi-sided, preferably rectilinear configuration. A pair of set screws 32 are also illustrated for securing the components to one another. Depending from the opposite side of member 18 from surface 20 is a generally centrally disposed pin 33 which is externally threaded.

The caudal component 14 includes a generally horizontally disposed member 34 having a lower surface 36 for engaging the upper surface of a vertebral body. Member 34, similarly as member 18, is generally semi-circular in shape. A pin 38 upstands from a central portion of member 34 and is externally threaded. A guide element 40 also upstands from member 34 adjacent one side thereof and has a cross-sectional shape complementary to the cross-sectional shape of recess 30 in cephalic component 12. Aligned with upstanding guide element 40 and depending from the same side of member 34 is an element 42 having two or more openings 44 for receiving screws 46 whereby the caudal component is fixed to a vertebral body. The screw openings 44 are similarly vertically and laterally spaced from one another and angled relative to one another.

The separating sleeve 16 is internally threaded at its opposite ends. Sleeve 16 has a generally hexagonal outer configuration facilitating rotation thereof. The threads of sleeve 16 and those of pins 33 and 38 are arranged such that rotating sleeve 16 in one direction causes separating movement of the components relative to one another, while rotating sleeve 16 in the opposite direction causes the components to move toward one another.

Each of the surfaces 20 and 36 is formed of a water-permeable or porous material. Each surface preferably comprises a coating applied to the metal of the component to a depth of about 0.5 mm to 3 mm. The porous nature of the surfaces facilitates osseous growth in those depressions or recesses of the surface that make contact with the bone. The materials of these surfaces may be hydroxyapatite, a ceramic, a polymer, metal or cobalt alloy. A porous surface formed of titanium alloys with a 5–50 micron rough surface, however, has been found satisfactory to facilitate biological integration. Moreover, the surfaces 20 and 36 are shaped complementary to the corresponding surfaces of the vertebral body to which they will be in contact. Thus, because the undersurface and upper surface of vertebral bodies are generally concave, the surfaces 20 and 36 are complementary shaped to the vertebral body surfaces and therefore are generally concave upwardly and downwardly, respectively, to ensure as much contact with the bone as possible. The cephalic and caudal components, as well as the sleeve 16 are preferably formed of titanium alloys, although other materials could be used, for example, chromium, molbydenum or cobalt alloys.

The securement elements 22 and 42 of the cephalic and caudal components are also shaped complementary to the lateral portions of the vertebral bodies to which the elements are attached and also may have a porous or water-permeable coating, similarly as members 18 and 34, to promote osseous growth. For example, with a radius equal to the length of the separating setscrew 16, the concave surface of securement elements 22 and 42 may range within 35°–45°. Also, for the same radius, the convex surface of the elements 22 and 42 in the vertebral direction, may range within 65°–75°.

Figure 2:
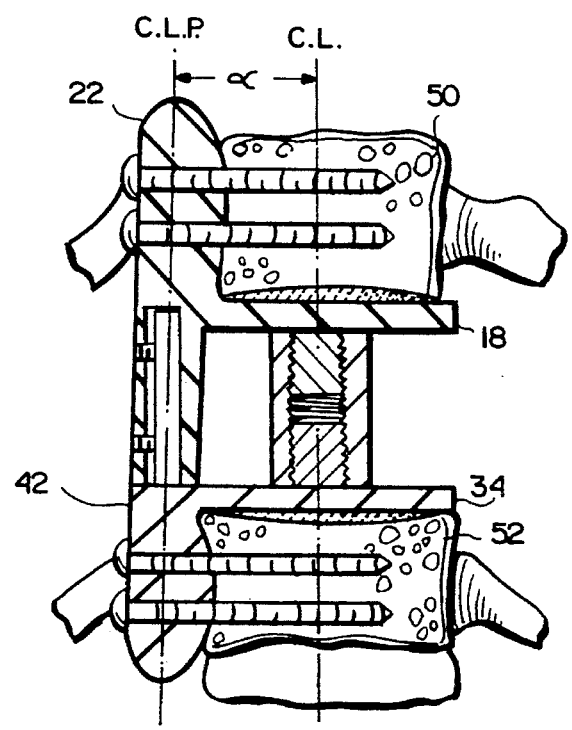
FIG. 2 is a cross-sectional view of the prosthesis of FIG. 1 in place and secured to vertebral bodies on opposite sides of a replaced vertebral body.

To use the prosthesis, the malignant or diseased vertebral body to be removed is exposed, using standard surgical procedures. The vertebral body is then completely removed, with all its disks, including intervertebral-cartilages. The components of the prosthesis are then preassembled prior to location in the vertebral column. Thus, upstanding element 40 is disposed in recess 30 and sleeve 16 is threaded onto both pins 33 and 38. This adjustable, but unitary assembly is disposed in the vertebral column with the members 18 and 34 lying in alignment with the upper and lower vertebral bodies 50 and 52 (FIG. 2). The sleeve 16 is then rotated to separate the members 18 and 34, causing the surfaces 20 and 36 to engage the generally complementary shaped undersurface and upper surface of the vertebral bodies 50 and 52, respectively. When the surfaces 20 and 36 engage the upper and lower vertebral bodies, screws 26 and 46 are inserted through the openings 24 and 44, respectively, and the cephalic and caudal components are secured to the upper and lower vertebral bodies, respectively. The set screws 32 are then tightened to fix the guide element 40 in the recess 30 and prevent relative rotation of the components. The prosthesis is then in final position, as illustrated in FIG. 2.

The present prosthesis is also readily removed from the vertebral column in the event that becomes necessary. To accomplish this, the screws 26 and 46 are then withdrawn and the set screws 32 are loosened. By rotating sleeve 16 in the opposite direction, the members 18 and 34 are drawn toward one another and away from the surfaces of the upper and lower vertebral bodies. The unitary assembly can then be readily removed.

Because of the different configurations and relative sizes of the adjoining vertebral bodies along different portions of the vertebrae, the present prosthesis may be provided in many different sizes but in the general shape described above.

Figure 3:
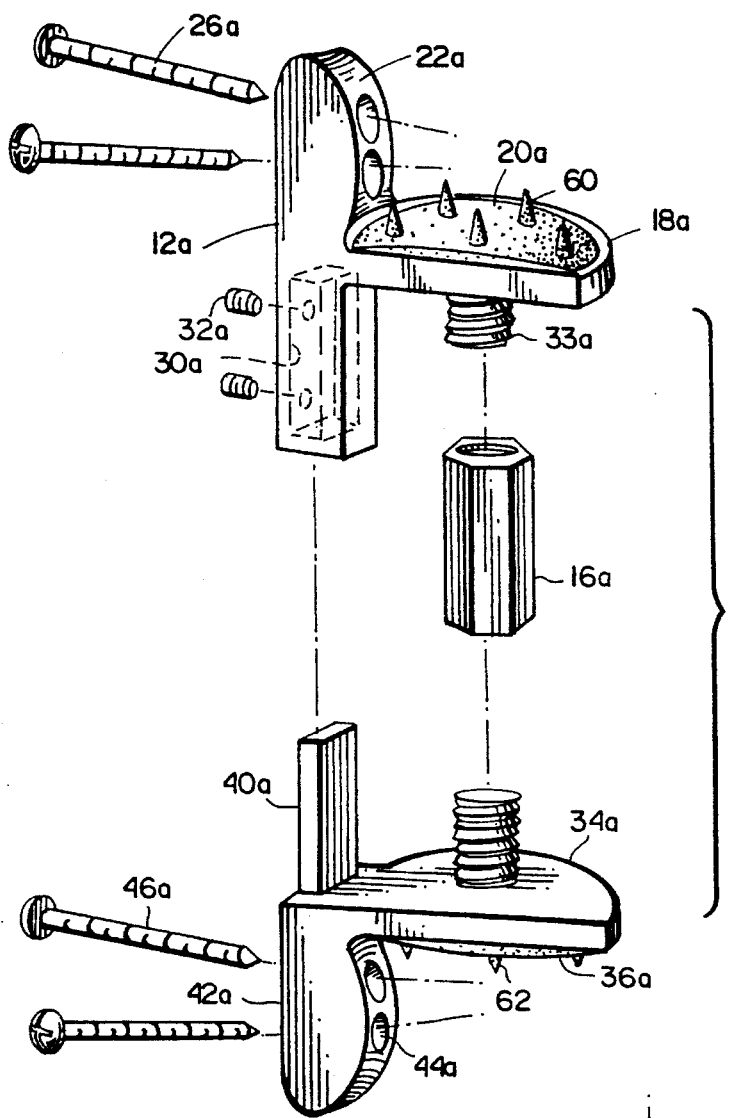
FIG. 3 is a view similar to FIG. 1 illustrating a further embodiment of the present invention.
Figure 4:
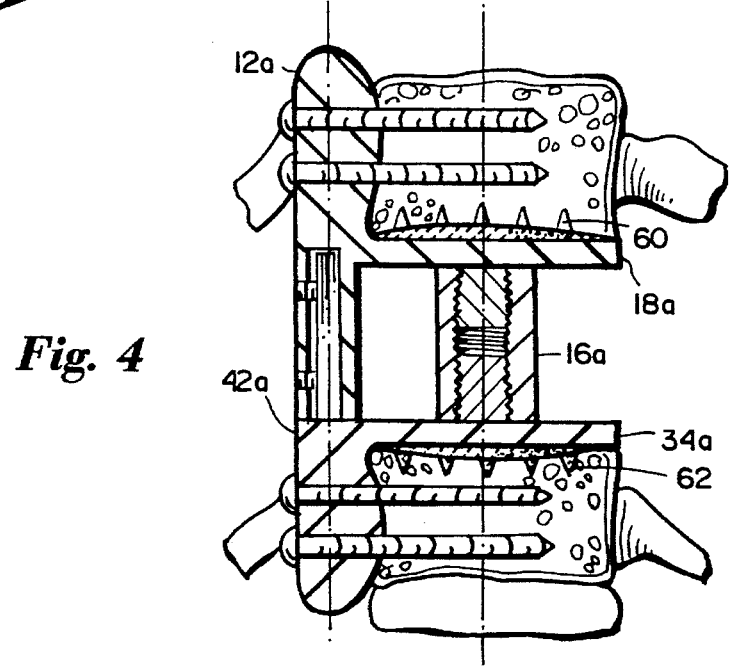
FIG. 4 is a view similar to FIG. 2 illustrating the securement of the prosthesis of FIG. 3 in the vertebral column.
Figure 5:
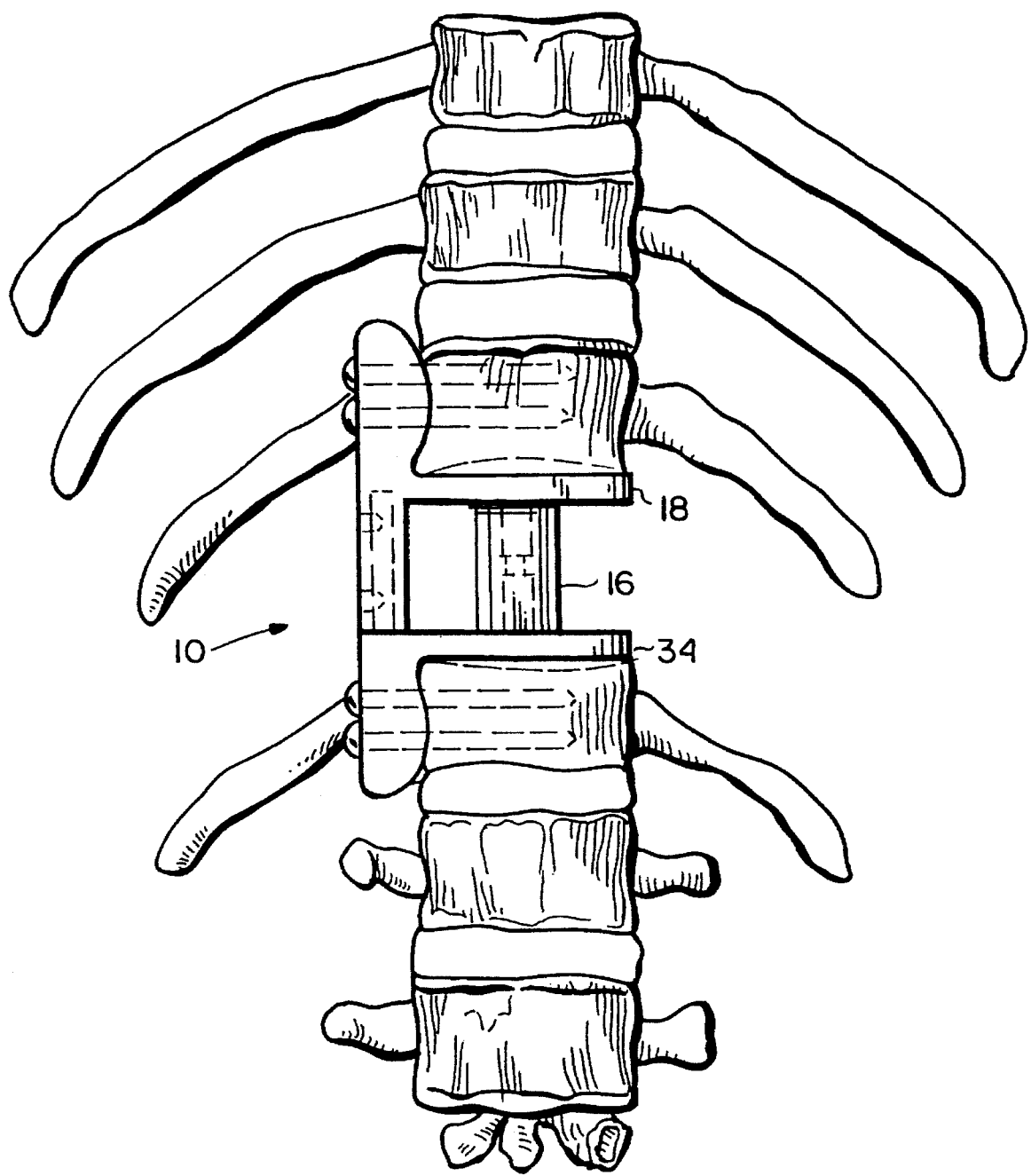
FIG. 5 is an elevational view of a vertebra with the prosthesis hereof in place.

Referring now to FIGS. 3 and 4, there is illustrated a further embodiment of the present prosthesis wherein like parts are designated by like reference numerals followed by the suffix "a". Thus, in this embodiment, the cephalic and caudal components are generally identical to those illustrated and described with respect to FIGS. 1 and 2, with the exception that the surfaces 20a and 36a are provided with projections for reception within the vertebral body to which the respective members 18a and 34a are connected. The projections 60 and 62 on the surfaces 20a and 36a, respectively, are preferably cone-shaped and spaced one from the other about the surface. Because the projections 60 and 62 will penetrate the vertebral body, they will assist in preventing relative movement between the vertebral bodies and the prosthesis. It will be appreciated that other shapes may be used for this purpose, for example, cylindrical pins. These projections form a crown on the surfaces 20a and 36a. When the prosthesis of this embodiment is used, the threading action of the sleeve 16a may be sufficient to drive the projections into the vertebral bodies. Otherwise, preformed holes may be formed in the surfaces of the vertebral bodies to receive the projections. The crowned components would be used for those patients having a better prognosis, whereas the non-crowned vertebral body prosthesis would be used for those patients with a poor prognosis.

It will be appreciated that the vertebral column has a wide base starting at the lower portion of the spine and that such width decreases as the vertebral column progresses upwardly toward the head. To accommodate this reduction in the lateral dimension from the base of the spine to the head, the securement and guide elements may have a centerline C.L.P. angled relative to a centerline C.L. through the vertebral column (see FIG. 2). Thus, the securement and guide elements may be aligned along centerline C.L.P. which makes a downwardly diverging angle α of about 5" with the centerline C.L. through the vertebral column. Consequently, the securement elements 22 and 42 may form angles of 85° and 95°, respectively, with the members 18 and 34. Note also that the screw holes 24 and 44 are vertically and laterally spaced and angled relative to one another in each securement element to provide a stronger and more stable securement.

Figure 6B:
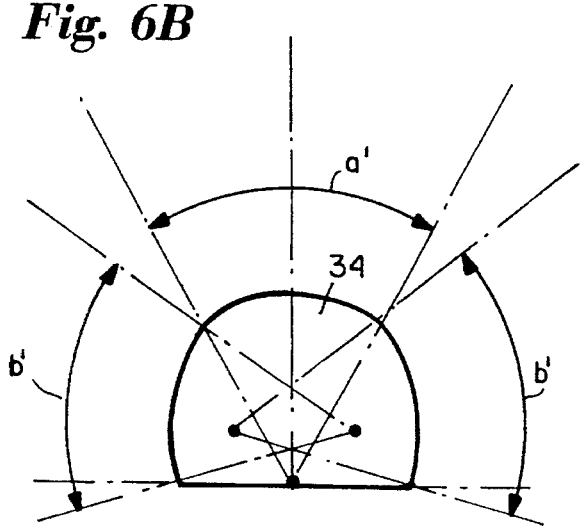
FIGS. 6A, 6B and 6C are schematic illustrations of the shape of the support members of the components in the various regions of the spine.
Figure 6C:
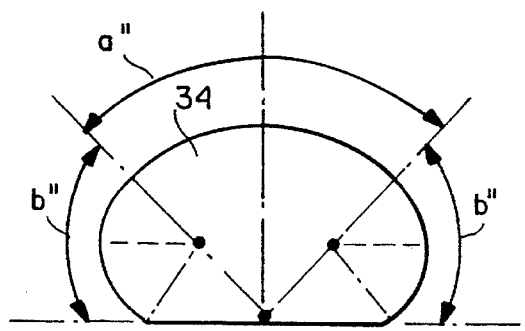
Figure 6A:
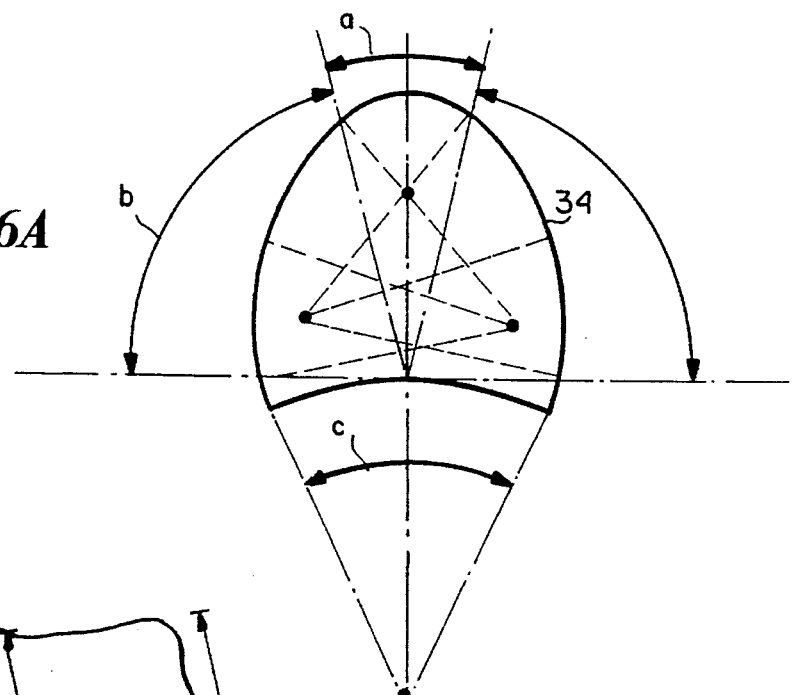

Further, the contours and dimensions of the members 18 and 34 of the cephalic and caudal components are different between the various regions of the backbone, i.e., the thoracic, thoracolumbar and lumbar regions, and may be different for conformance to the contours and dimensions of the vertebral bodies in the various regions within each region. For example, in the thoracic region, and with a radius equal to the height of the vertebral body being replaced, i.e., approximately the length of the separating setscrew, the member 18 or 34 may have, as illustrated in FIG. 6A, a front circle segment a of 30°, left and right lateral circle segments b of 75°, and a back arch c of 50°. The back arch could be a straight line tangent to the arch. In the thoracolumbar region, the members 18 or 34 may have a front circle segment a' 76°, the left and right lateral circle segments b' 54° and the back arch c' a straight line. For the lumbar region, the front circle segment a" may be 90°, the left and right circle segments b" 90°–110° and the back arch c" a straight line, the radius being equal to the length of the separating setscrews for the front circle segment a" and 50° of the separating setscrew length for the left and right lateral circle segments b" as illustrated in FIG. 6A. As a generalization, however, the circle segments forming the bases of both the cephalic and caudal components are the same in each of the three regions but different from one another whereas the radius of the circle segments is different within each region.

Figure 7:
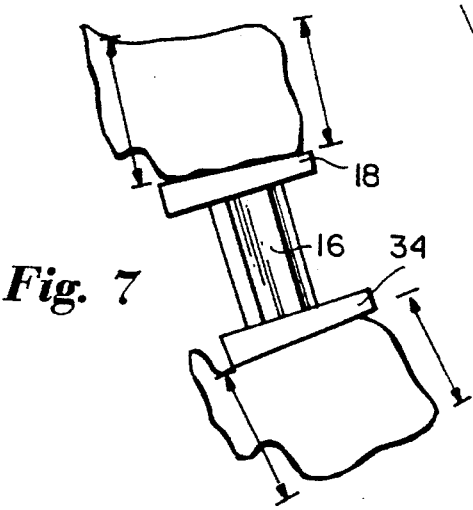
FIG. 7 is a side elevational view of a portion of the thoracic region of the spine with the prosthesis applied.
Figure 8:
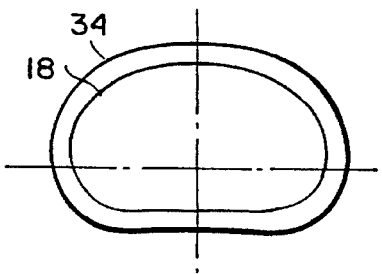
FIG. 8 is a schematic illustration not to scale of the superposition of the support members of the prosthesis overlying one another illustrating their different dimensions.

Additionally, the horizontal dimensions of the members of the preassembled prosthesis for replacement of a specified vertebral body in one of the regions are different. Thus, as illustrated in FIG. 8, the upper member associated with the cephalic component is smaller in lateral and front-to-back dimensions than the lower member of the adjoining caudal component, although the contours are generally the same. Also, because the back height of a vertebral body is greater than the front height, e.g., in the thoracic region, the vertical height or depth of the members 20 and 34 may be different to complement for that difference in height. That is, the back part of the members 20 and 34 may be thicker than the front part as illustrated in FIG. 7.

While the invention has been described with respect to what is presently regarded as the most practical embodiments thereof, it will be understood by those of ordinary skill in the art that various alterations and modifications may be made which nevertheless remain within the scope of the invention as defined by the claims which follow.

What is claimed is:

1. A prosthesis for replacing a vertebral body in the spine of a human being comprising:

a cephalic component including a generally horizontally disposed member having an upper surface for engaging the underside of an upper vertebral body;

a caudal component including a generally horizontally disposed member having a lower surface for engaging the upper side of a lower vertebral body; and means for connecting said components in selected adjusted positions relative to one another, said connecting means including a sleeve having an axis and disposed between and rotatable relative to said components, at least one of said components and said sleeve having complementary threaded parts such that rotation of said sleeve in at least one rotary direction adjusts the spacing between said members in direct response to rotation of said sleeve;

said cephalic element having an element upstanding from and on one side of said member thereof for securement to a lateral side of the upper vertebral body, said caudal component having an element depending from and on one side of said member thereof for securement to a lateral side of the lower vertebral body;

a first guide element depending from said cephalic component and a second guide element upstanding from said caudal component, said guide elements being spaced laterally from said connecting means, one of said guide elements having a recess and another of said guide elements being receivable in said recess to enable movement of said members toward and away from one another and prevent rotational movement of said components relative to one another, said guide elements and said securement elements lying in generally linear alignment with one another and in a plane passing through said axis when said components are connected to one another;

whereby stabilization of and support for the spine is afforded.

2. A prosthesis according to claim 1 wherein another of said components and said sleeve have complementary threaded parts such that rotation of said sleeve in opposite rotary directions respectively increases and decreases the spacing between said members in direct response to rotation of said sleeve.

3. A prosthesis according to claim 1 wherein said one component has a threaded pin projecting from the member of said one component toward another component, said sleeve having an internal thread at one end for threaded engagement with said threaded pin.

4. A prosthesis according to claim 1 wherein said upper surface and said lower surface are formed of a material for the promotion of osseous growth.

5. A prosthesis according to claim 4 wherein said surfaces are formed of a porous material.

6. A prosthesis according to claim 1 wherein at least one of said upper surface and said lower surface has a plurality of projections spaced from one another for penetration within an adjacent vertebral body.

7. A prosthesis according to claim 1 wherein said upper and lower surfaces are convex for engaging in generally complementary-shaped recesses of the respective adjacent vertebral bodies.

8. A prosthesis according to claim 1 wherein said upper and lower surfaces are convex for engaging in generally complementary-shaped recesses of the respective adjacent vertebral bodies.

9. A prosthesis according to claim 1 wherein each of said securement elements has a pair of openings for receiving screws for securing the components to the adjacent vertebral bodies, said openings being angularly related to one another such that screws receivable in the openings are angularly related to one another.

* * * * *